(12) United States Patent
Sendai

(10) Patent No.: US 6,796,938 B2
(45) Date of Patent: Sep. 28, 2004

(54) IMAGE OBTAINING METHOD AND APPARATUS OF AN ENDOSCOPE APPARATUS

(75) Inventor: Tomonari Sendai, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 92 days.

(21) Appl. No.: 10/132,288

(22) Filed: Apr. 26, 2002

(65) Prior Publication Data
US 2002/0161283 A1 Oct. 31, 2002

(30) Foreign Application Priority Data

Apr. 27, 2001 (JP) .......................... 2001-132120
Mar. 27, 2002 (JP) .......................... 2002-089109

(51) Int. Cl.[7] .............................................. A61B 1/045
(52) U.S. Cl. ...................... 600/109; 600/160; 600/476; 348/68
(58) Field of Search .................................. 600/160, 109, 600/118, 476–478; 348/76, 68

(56) References Cited

U.S. PATENT DOCUMENTS 6,524,858 B1 * 2/2003 Zelmanovic et al. ......... 436/10
2002/0138008 A1 * 9/2002 Tsujita et al. ................ 600/473

* cited by examiner

Primary Examiner—John P. Leubecker
(74) Attorney, Agent, or Firm—Sughrue Mion, PLLC

(57) ABSTRACT

An image obtaining method and apparatus for an endoscope apparatus wherein reductions to the gradations of the image data borne by the analog signal are suppressed and digital values having a narrower dynamic range are obtained when the photoelectrically converted and outputted analog signal is converted to digital values. A living tissue is irradiated by an illuminating light and an excitation light, which are each emitted at different timings; whereupon a fluorescent image formed of the fluorescent light emitted from the living tissue and a standard image formed of the reflected light reflected from the living tissue are received, converted to respective analog signals, and outputted by the same photoelectric converting element. In converting these analog signals to digital values, the analog signal representing the fluorescent image is amplified by a larger gain than that representing the standard image.

9 Claims, 6 Drawing Sheets

IMAGE OBTAINING METHOD AND APPARATUS OF AN ENDOSCOPE APPARATUS

BACKGROUND OF THE INVENTION

1. Field of the Invention

The present invention relates in general to a image obtaining method and apparatus for an endoscope apparatus, and in particular to an image obtaining method and apparatus for an endoscope apparatus wherein a low-intensity fluorescent light image and a high-intensity standard image are received by use of the same photoelectrical converting element.

2. Description of the Related Art

Endoscope apparatuses for observing living tissues within a body cavity are widely known, and there are in wide use today electronic endoscope apparatuses wherein an illuminating light such as a white light or the like for observing living tissue is projected into a subject body cavity and an image of the living tissue illuminated thereby is obtained by use of a CCD element or the like, and this image is observed on a television screen. Further, the living tissue within the body cavity is not only illuminated by an illuminating light such as a white light or the like and observed: endoscope apparatuses that obtain a visible image formed based on a standardized fluorescent light intensity, which represents the ratio between the intensity of the fluorescent light near the wavelength range of 480 nm and the intensity of the fluorescent light in the wavelength range spanning from 430–730 nm emitted from the living tissue within the body cavity upon the irradiation thereof by an excitation light of a wavelength near 410 nm; or a visible image based on a fluorescent light yield ratio, which represents the ratio between the intensity of the fluorescent light emitted from the living tissue within the body cavity upon the irradiation thereof by the aforementioned excitation light and the intensity of the near infrared light reflected from the aforementioned living tissue upon the irradiation thereof by a near infrared light, which is a reference light, for use in diagnosing the tissue state of a target tissue have also been proposed. Note that the excitation light is readily absorbed by the living tissue, and because it is difficult to use the excitation light intensity received by the target tissue for measurement, near infrared light or a red light or the like, which is not readily absorbed by the living tissue, is employed as a reference light, and the excitation light intensity received by the living tissue is measured.

Because there is a large difference between the light intensity of a standard image formed of the high-intensity illuminating light that has been reflected from a living tissue that has been irradiated thereby and a fluorescent image formed of the low-intensity fluorescent light emitted from a living tissue upon the irradiation thereof by an excitation light, if, for example, these two images were to be time divided and obtained by the same image obtaining element, a dynamic range on the order of 90 dB (approximately 65000 gradations) would be required. However, the dynamic range of a currently available typical photoelectrical converting element is 60 dB (approximately 1000 gradations); therefore, an operation wherein, for example, a standard image only is passed through a light reducing filter and the light passing therethrough is received; and the standard image and the fluorescent image are both within a dynamic range below 60 dB and the light thereof is received; wherein the standard image and the fluorescent image received thereby are each photoelectrically converted and obtained as an analog signal, respectively, is performed. Then, these analog signals are converted to digital values after being amplified by a roughly fixed predetermined gain, and these digital values are used to form a visible image of the aforementioned living tissue and said visible image is observed, or the fluorescent light yield, the standardized fluorescent light intensity or the like is obtained and a visible image representing the tissue state of the aforementioned living tissue is formed and a diagnosis is carried out.

On the other hand, research and development of photoelectrical converting elements having a dynamic range of 90 db is also progressing, and if a photoelectric converting element having a dynamic range enlarged to this extent is employed, the standard image and the fluorescent image can be received by the same photoelectric converting element within the dynamic range thereof without the standard image having to first be passed through a light reducing filter or the like, and the light intensity of the standard image received by the photoelectric converting element becomes higher. In this manner, the ratio of photon noise generated in proportion to the square root of the received light intensity can be largely reduced, and because the S/N ratio of the standard image can be improved, it is desirable that a photoelectric converting element having an enlarged dynamic range such as this be utilized in an endoscope apparatus.

However, the analog signal obtained by a photoelectric converting element having a wide dynamic range such as this has a wide dynamic range, and the circuitry for processing said wide dynamic range analog signal, such as an A/D converting circuit, a computational circuit or the like, must also have the same wide dynamic range (such as 90 dB or 16 bits), and there is a problem in that it is difficult to construct such circuitry. That is to say, a circuit having a wide dynamic range such as this and the elements configuring said circuit are not common; they are extremely expensive; particularly in the case of disposing a photoelectric converting element having a wide dynamic range (e.g., 90 dB) in the distal end of an endoscope apparatus, in which signals are transmitted through a narrow tube, there is the fear of a problem due to noise becoming mixed in with the signal during transmission.

SUMMARY OF THE INVENTION

The present invention has been developed in consideration of the circumstances described above, and it is a primary objective of the present invention to provide an image obtaining method and apparatus for an endoscope apparatus, which are capable of converting a photoelectrically converted and outputted analog signal to a digital value having a narrower dynamic range, while suppressing the reduction of the gradations of said analog signal, whereby the mixing of noise with said digital value can be suppressed, and the cost of the apparatus can be reduced.

The image obtaining method of the endoscope apparatus according to the present invention comprises the steps of: irradiating a living tissue with an illuminating light and an excitation light, each of which is emitted at a mutually different timing; receiving, by use of the same photoelectric converting element, a fluorescent image formed of the fluorescent light emitted from the living tissue upon the irradiation thereof by the excitation light and a standard image formed of the reflected light reflected from the living tissue upon the irradiation thereof by the illuminating light; photoelectrically converting the standard image and the fluorescent image received thereby, to obtain each as respective analog signals; converting these analog signals to respective digital values; and outputting these digital values as an image signal; wherein, the analog signal representing the fluorescent image is converted to digital values after being amplified by a larger gain than the gain utilized in amplifying the analog signal representing the standard image.

The image obtaining apparatus of the endoscope apparatus according to the present invention comprises: an illuminating means for irradiating a living tissue with an illuminating light and an excitation light, each of which is emitted at a mutually different timing; a light receiving means for receiving a fluorescent image formed of the fluorescent light emitted from the living tissue upon the irradiation thereof by the excitation light, and a standard image formed of the reflected light reflected from the living tissue upon the irradiation thereof by the illuminating light, and photoelectrically converting the standard image and the fluorescent image received thereby to respective analog signals and outputting said analog signals; an amplifying means for amplifying said analog signals; and an A/D converting means for converting the amplified analog signals to respective digital values; wherein, the amplifying means amplifies the analog signal representing the fluorescent image by a larger gain than that utilized in amplifying the analog signal representing the standard image.

It is preferable that the gain of the amplifying means be set so that the largest value of the analog signal representing the fluorescent image becomes substantially equivalent to the largest value of the analog signal representing the standard image.

The amplifying means comprises a floating diffusion amplifier for converting to voltages the analog signal representing the fluorescent image outputted from the light receiving means, and an A/D conversion gain adjusting amplifier for amplifying the output voltage from said floating diffusion amplifier; wherein the gain thereof can be the gain of the floating diffusion amplifier and/or the A/D conversion gain adjusting amplifier. Here, the referent of the "and" of the expression "the gain can be the gain of the floating diffusion amplifier and/or the A/D conversion gain adjusting amplifier" is that the gain of the amplifying means can be the gain of the floating diffusion amplifier multiplied by the gain of the A/D conversion gain adjusting amplifier.

The gain is set based on respective histograms representing the distribution of the light intensity of the fluorescent image and the standard image, which have been formed using digital values; so that the largest value of each of the respective histograms can be substantially equal.

The gain can be selected from among a plurality of preset stepped values.

As to the technique for amplifying the analog signal representing the fluorescent image by a larger gain than that utilized to amplify the analog signal representing the standard image, a method such as that described below can be employed.

That is to say, a method wherein: the gain used when amplifying the analog signal representing the fluorescent image (hereinafter referred to as the fluorescent image gain) and the gain used when amplifying the analog signal representing the standard image (hereinafter referred to as the standard image gain) are set so that the fluorescent image gain is larger than the standard image gain; the fluorescent image gain is employed when the analog signal representing the fluorescent image is to be amplified; and the standard image gain is employed when the analog signal representing the standard image is to be amplified, can be employed. This means differs from a means such as an automatic gain controller (AGC), which automatically adjusts the amplification gain of the analog signal representing a photoelectrically converted image converted after the input of the image data representing the image before the photoelectrical conversion thereof, based on the input image data.

Further, according to the image obtaining method and apparatus for an endoscope apparatus of the present invention, an A/D converting means for converting the analog signal representing the fluorescent image to digital values having a smaller input range than that of the analog signal representing the standard image, can be provided instead of the means for amplifying the analog signal representing the fluorescent image by a larger gain than that utilized to amplify the analog signal representing the standard image.

It is preferable that this A/D converter be provided so as to be capable of switching the input range so that the largest value of the digital values representing the fluorescent image becomes substantially equal to the largest value of the digital values representing the standard image.

The input range can be set based on respective histograms representing the distribution of the light intensity of the fluorescent image and the standard image, which have been formed using digital values; so that the largest value of each of the respective histograms can be substantially equal.

The input range can be selected from among a plurality of preset stepped values.

The fluorescent image can be a fluorescent image formed of a plurality of mutually different wavelength ranges of fluorescent light, into each of which fluorescent light has been divided spectrally in a time division manner.

The illuminating light can be light containing wavelengths within the near infrared wavelength range.

It is preferable that the A/D converter be a means for converting the analog signal outputted from the amplifying means to a digital value containing 14 bits or less of data.

It is preferable that the light receiving means be a charge multiplying photoelectric converting element.

Note that the input range refers to the input range (full-scale input range) of the maximum analog signal value capable of being A/D converted by the A/D converter.

According to the photographing method and apparatus of the endoscope apparatus of the present invention: in outputting an image signal formed of the digital values, which the respective analog signals representing a fluorescent image and a standard image that have been received and photoelectrically converted at the same photoelectric converting element, have been converted to, because the analog signal representing the fluorescent image (hereinafter referred to as the fluorescent image analog signal), which has been received at a low intensity is formed of small signal values, is amplified by a gain larger than that used for amplifying the analog signal representing the standard image (hereinafter referred to as the standard image analog signal), which has been received at a high-intensity and is formed of large signal values, and then converted to digital values, the fluorescent image analog signal can be correlated to a higher order digital values region and converted; compared to cases in which the fluorescent image analog signal and the standard image analog signal have been amplified by the same gain, the fluorescent image analog signal can be converted to digital values wherein the losses in the gradations of the image data borne by the fluorescent image analog signal can be suppressed. That is to say, the fluorescent image analog signal can be represented as digital values divided into quantization units of a smaller signal level than those of the standard image analog signal.

Further, for cases in which the dynamic range of the digital values has been set so as to be of a narrower dynamic range than the dynamic range of the values of the analog signals, the fluorescent image analog signal can be converted to digital values of a narrow dynamic range wherein the reduction of the gradations can be suppressed, and the circuitry for processing these digital signals can be simpler than that used for processing the signals having a dynamic range similar to those of the analog signals; because the circuitry for processing these digital values can be configured so as to have a narrower dynamic range, the cost of the apparatus can be reduced, and an effect whereby the noise becoming mixed with the signal within such circuitry having a narrow dynamic range is suppressed can be expected.

Note that although there is a loss of gradations in the standard image represented by the standard image analog signal when said analog signal is converted to digital values, because the standard image analog signal has higher gradations formed of larger signal values than those of the fluorescent image analog signal, even if the gradations of the image data borne by the standard image analog signal undergo reduction somewhat, there will be little reduction of the quality of the image data thereof; further, there will also be almost no adverse effect on the accuracy of the computations performed to obtain the fluorescent light yield and the like.

Here, if the amplifying means is a means that sets the gain thereof so that the largest value of the fluorescent analog signal becomes substantially equal to the largest value of the standard image analog signal, because the fluorescent image analog signal, which is formed of smaller signal values than those of the standard image analog signal, can be amplified to a size equivalent to that of the standard image analog signal and then converted to digital values, the fluorescent image analog signal can be converted to digital values in a manner that ensures the suppression of the reduction of the gradations in the image data borne by said fluorescent image analog signal.

Further, if the amplifying means is provided with a floating diffusion amplifier for converting to voltages the analog signals outputted from the light receiving means, and an A/D conversion gain adjusting amplifier for amplifying the output voltage of said floating diffusion amplifier, and the gain is made to be the gain of the floating diffusion amplifier and/or the A/D conversion gain adjusting amplifier, the fluorescent image analog signal can be more easily amplified by a gain larger than that by which the standard image fluorescent image analog signal is amplified.

Note that if the gain is set, based on the respective histograms representing the light intensity distributions of the fluorescent image and the standard image and which have been formed utilizing digital values, so that the largest value of the light intensity represented by each histogram is substantially equal, the reduction of the gradations of the fluorescent image occurring when the digitization thereof is performed can be positively suppressed to be less. Further, if the gain is selected from among a plurality of preset stepped values, changing the gain can be performed by a simpler circuitry.

Further, according to another photographing method and apparatus for an endoscope apparatus of the present invention, an A/D converter has been provided which converts the fluorescent image analog signal to a digital value with a narrower input range than that for the standard image analog signal, instead of the amplifying means that amplifies the fluorescent image analog signal with a larger gain than that for the standard image analog signal. Thereby, the fluorescent image analog signal can be converted to digital values corresponding to a range of a higher order. Compared to the case in which the fluorescent image analog signal and the standard image analog signal are converted at the same input range, the fluorescent image analog signal can be converted to digital values while suppressing the loss of gradations in the image data borne thereby. That is, the fluorescent image analog signal can be expressed as a digital value which has been divided into signal levels having a lower quantization unit than that of the standard image analog signal.

Note that in the case that the dynamic range of the digital values is set to be narrower than the dynamic range of the analog signals, the fluorescent image analog signals can be converted to digital values having a narrower dynamic range while suppressing the reduction in gradation thereof. Therefore, the circuitry to process these digital values can be constructed of simpler circuits having a narrower dynamic range than that of the circuits having the dynamic range of the analog signals, whereby the cost of the apparatus can be reduced. Further, an effect can be expected that the noise mixed in with the signals will be reduced by the use of a circuit structure having a narrow dynamic range.

Further, if the A/D converter be provided so as to be capable of switching the input range so that the largest value of the digital values representing the fluorescent image becomes substantially equal to the largest value of the digital values representing the standard image, because the fluorescent image analog signal, which is formed of signal values smaller than those of the standard image analog signal, can be converted to digital values of the same size as those of the standard image signal, said fluorescent image analog signal can be converted to digital values wherein the reductions occurring in the gradations of the image data represented by said fluorescent image analog signal can be more positively suppressed.

Still further, if the input ranges are set based on the respective histograms, which have been formed using digital values and which represent the respective distributions of the light intensity of the fluorescent image and the standard image, so that the largest value of the light intensity distribution occurring within each said histogram become substantially equal, the reduction of the gradations occurring in the fluorescent image when the digitization thereof is performed can be positively suppressed to be less; further, if this input range is selected from among a plurality of preset stepped values, changing said input range can be performed more simply.

Note that if the fluorescent image is an image formed of a plurality of mutually different wavelength ranges of fluorescent light, into each of which fluorescent light has been divided spectrally in a time division manner, and the standard image is an image containing wavelengths of light within the near infrared wavelength range, the application thereof in fluorescent image diagnosis becomes easier.

Further, if the A/D converter is a means for converting the analog signal outputted from the amplifying means to a digital value containing 14 bits of data or less, the circuitry down line from the A/D converter can be easily configured.

Still further, if the light receiving means is a charge multiplying photoelectric converting element, the standard image can be obtained as a standard image analog signal having a higher S/N ratio.

DESCRIPTION OF THE PREFERRED EMBODIMENTS

Figure 1:
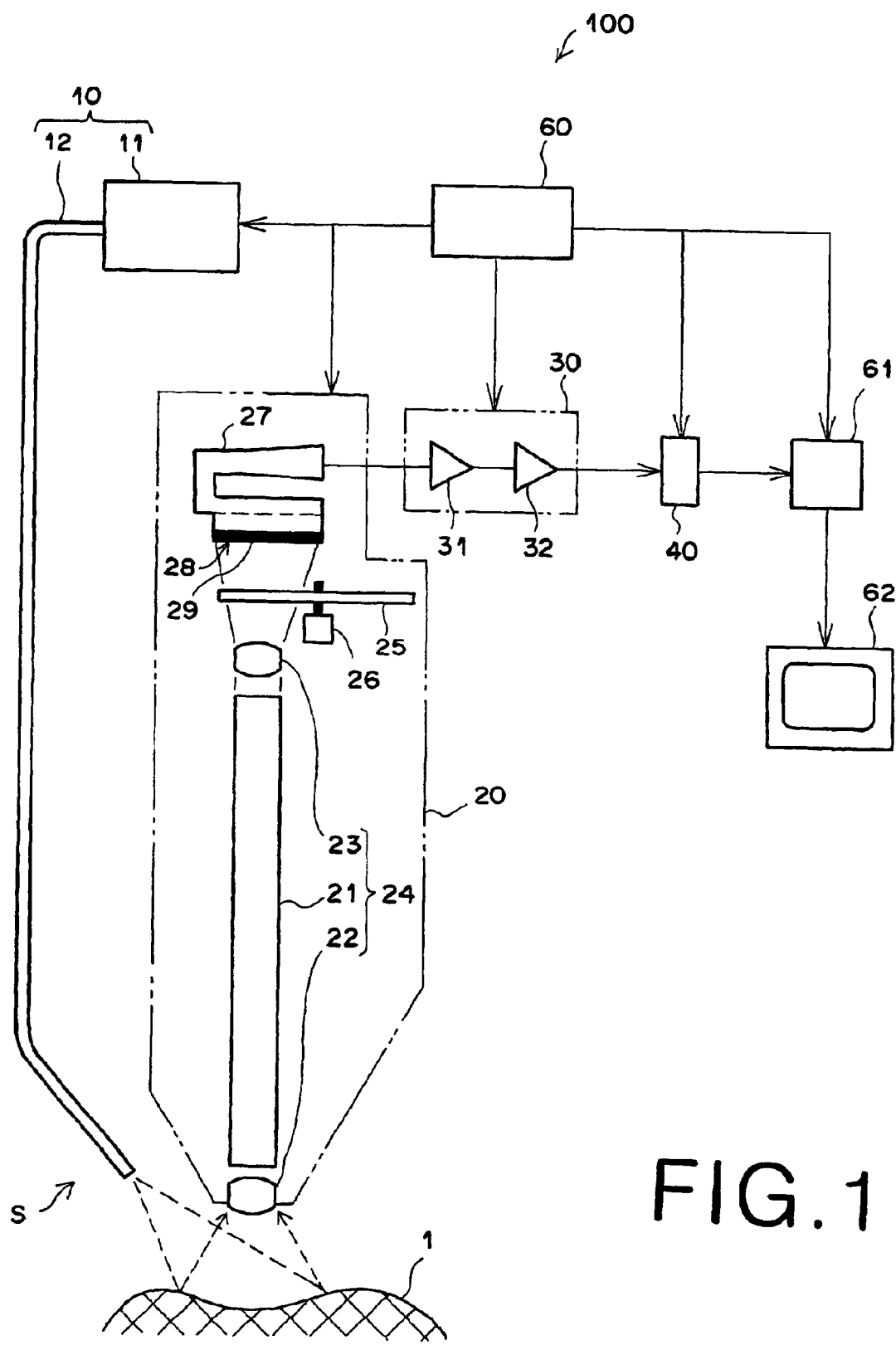
FIG. 1 is a block diagram of the configuration of the main part of the first embodiment of the present invention.
Figure 2:
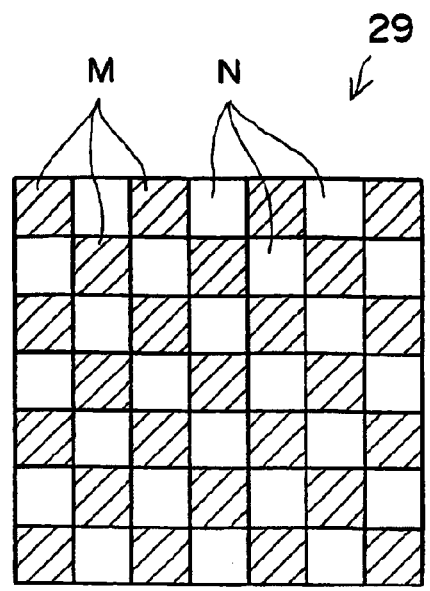
FIG. 2 is a magnified view of the configuration of a mosaic filter.
Figure 3:
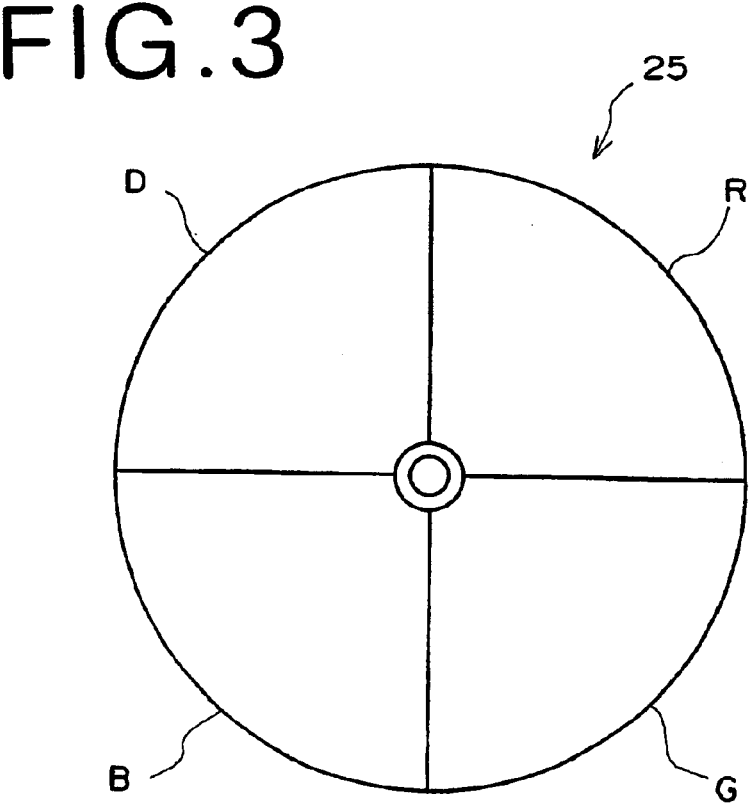
FIG. 3 is a magnified view of the configuration of a rotating filter.
Figure 4:
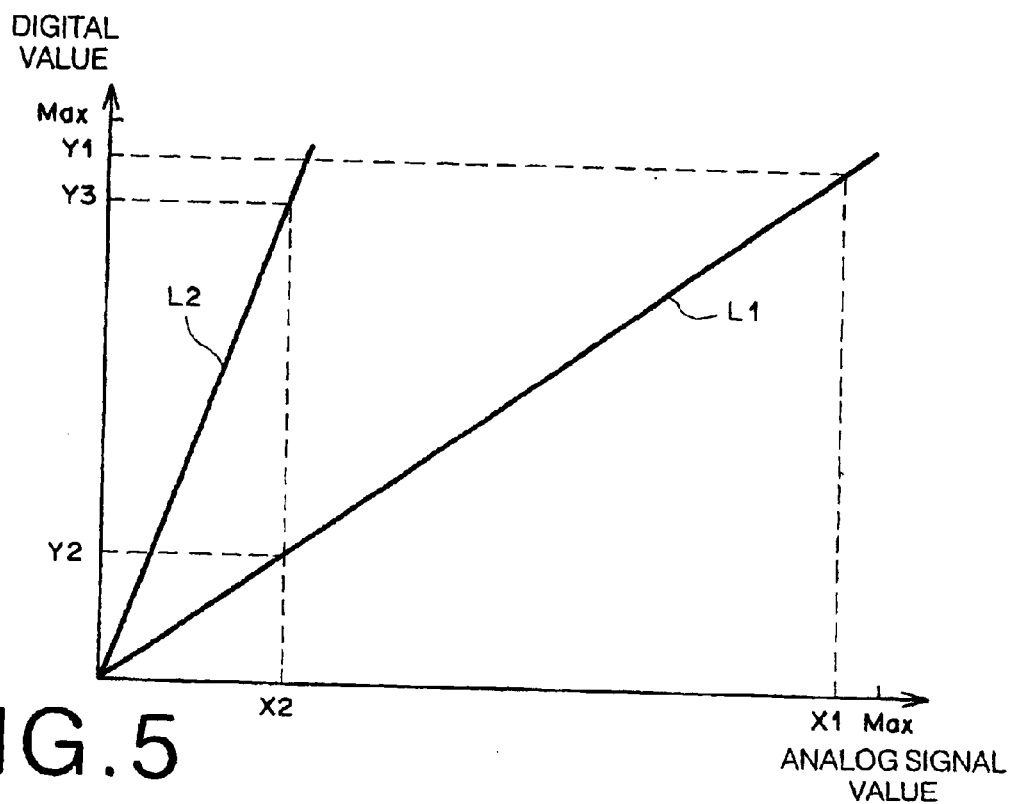
FIG. 4 is a graph illustrating the relationship between an analog signal and the digital values to which said analog signal is converted.

Hereinafter the preferred embodiments of the present invention will be explained with reference to the attached drawings. FIG. 1 is a block diagram of the configuration of the main part of the first embodiment of an endoscope apparatus implementing the image obtaining method and apparatus according to present invention. FIG. 2 is a magnified view of the configuration of a mosaic filter. FIG. 3 is a magnified view of the configuration of a rotating filter. FIG. 4 is a graph illustrating the relation between an analog signal and the digital values to which said analog signal has been converted. The endoscope apparatus according to the first embodiment comprises: a photoelectric converting element provided within the main body of the endoscope apparatus; wherein an image propagated along an image fiber from the distal end portion of the endoscope is received by this photoelectric converting element, and a visible image representing a standard fluorescent light intensity is superposed onto a standard observation image obtained by illumination with a white light and displayed.

The endoscope apparatus 100 according to the present invention comprises: an illuminating means 10 for irradiating a living tissue 1 with an illuminating light and an excitation light, each being emitted at a mutually different timing; a light receiving means 20 for receiving a fluorescent image formed of the fluorescent light emitted from the living tissue upon the irradiation thereof by the excitation light and a standard image (a standard observation image) formed of the reflected light reflected from the living tissue upon the irradiation thereof by the illuminating light, and photoelectrically converting the aforementioned standard image and the aforementioned fluorescent image received thereby to respective analog signals and outputting said analog signals; an amplifying means 30 for amplifying the analog signals; and an A/D converting means 40 for converting the amplified analog signals from the amplifying means 30 to respective digital values, each containing 12 bits of data.

The illuminating means 10 comprises a light source apparatus 11 equipped with a gallium nitride semiconductor laser (GaN-LD) that emits pulse type excitation light having a wavelength near 410 nm, and a white light source that emits a white light, which serves as an illuminating light whereby each of the aforementioned excitation light and illuminating light are emitted at mutually different timings, and a light guide 12 for propagating each of the aforementioned excitation light and illuminating light emitted from the light source apparatus 11 to the distal end S of the endoscope.

The light receiving means 20 comprises: an image propagation optical system 24 formed of a focusing optical system 22 and a focusing optical system 23, each of which is disposed at one of the two ends of an image fiber 21; a rotating filter 25 formed of a plurality of filters combined into a disk shaped integral unit; a motor 26 for rotating this rotating filter; and a charge multiplying photoelectric converting element 27, which has a dynamic range of 90 dB and is formed of a plurality of pixels, for receiving and converting the image propagated and focused by the image propagation optical system 24; wherein the image passing through the image propagation optical system 24 and the rotating filter 25, and focused the light receiving surface 28 of the photoelectric converting element 27 is photoelectrically converted and outputted as an analog signal.

Note that a mosaic filter 29, as shown in FIG. 2, comprising narrow band transmitting micro filters M, which transmit only light having a wavelength near 480 nm, and wide band transmitting filters N, which cut off the excitation light and transmit light having a wavelength in the visible spectrum exceeding the wavelength of the excitation light, which are disposed on alternate pixels, is disposed on the light receiving surface 28 of the photoelectric converting element 27, which is formed of a plurality of pixels.

Further, the rotating filter 25 comprises 3 color filters (color filter R, color filter G, color filter B), each for transmitting one of the respective three colors red, blue and green, and a fluorescent light transmitting filter D for transmitting fluorescent light.

The amplifying means 30 is a means for amplifying the analog signal representing the fluorescent image outputted from the light receiving means 20 by a larger gain than that used for amplifying the analog signal representing the standard image; comprising a floating diffusion amplifier 31 (hereinafter referred to as an FD amp 31) that converts the analog signals (electrical charges) outputted from the light receiving means 20 to voltages; and an A/D conversion gain adjusting amplifier 32 that amplifies the output voltage of the FD Amp 31, wherein the gain of the amplifying means 30 is determined by the settings of the FD amp 31 and the A/D conversion gain adjusting amplifier 32. These gain settings are performed in synchronization with the timing of the gain setting signals outputted from a control means 60.

The endoscope apparatus 100 further comprises: a computed visible image outputting means 61, into which the digital values outputted from the A/D converting means 40 are inputted, for performing computations to obtain a standardized fluorescent light intensity and outputting as a visible image signal the digital values representing the standardized fluorescent light intensity obtained thereby; and a display device 62 for displaying the visible image signal outputted from the computed visible image outputting means 61.

The control means 60 controls the overall operation of the apparatus (e.g., the emission of the illuminating light and the excitation light, the rotation of the rotating filter 25, the photoelectrical conversion performed by the light receiving means 20, the output of the gain setting signals from the control means 60, etc.) and the timing and the like of each operation so that the image representing the standardized fluorescent light intensity is superposed on a standard image and displayed on the display device 62.

Note that according to the configuration described above, the circuitry of the computed visible image outputting means 61, which is down line from the A/D converting means 40, is formed of circuits and elements having a narrower dynamic range than the than the analog signals outputted from the light receiving means 20. That is to say, the dynamic range of the output of the light receiving means 20 is set so as to be wider than that of the circuitry and elements forming the computed visible image outputting means 61.

Next, the operations occurring in the above-described first embodiment will be explained.

A white light, which is an illuminating light, is emitted from the illuminating means 10, passes through the light guide 12 and is projected onto a living tissue 1; the illuminating light reflected from the living tissue 1 upon the irradiation thereof by the illuminating light passes through the image propagating optical system 24, the filter R of the rotating filter 25 and the mosaic filter 29, and is focused and received as a standard image on the light receiving surface 28. The received standard image is photoelectrically converted by the photoelectric converting element 27 and outputted from the light receiving means 20 as a standard image analog signal representing a standard image.

The standard image analog signal outputted from the light receiving means 20 is inputted to the amplifying means 30, and after being converted to voltages by the FD amp 31, is amplified and outputted by the A/D conversion gain adjusting amplifier 32. The gain of the amplifying means 30 at this time is set in synchronization with the timing of the gain setting signals outputted from the control means 60. Note that the setting of the gain of the FD amp 31 is performed by a charge-to-voltage converting MOSFET voltage gain change.

The amplified standard image analog signal outputted from the amplifying means 30 is inputted to the A/D converting means 40, and after being converted thereby to a 12-bit standard image digital signal representing the standard image, is input to the computed visible image outputting means 61.

The computed visible image outputting means 61 into which the standard image digital signal has been inputted records only the digital signal obtained after said inputted standard image digital signal has been passed through the wide band transmitting filter N of the mosaic filter 29; the standard image digital signal that passes through the narrow band transmitting filter M is not utilized.

The same operation whereby the standard image that has passed through the filter R and been focused on the light receiving surface 28 is recorded within the computed visible image outputting means 61 as a standard image digital signal is performed for the standard image that passes through each of the filter G and the filter B and is focused on the light receiving surface 28; whereby a standard image digital signal representing a three color, red, green and blue standard image is recorded within the computed visible image outputting means 61.

Next, an excitation light is emitted from the illuminating means 10, passes through the light guide 12 and is projected onto a living tissue 1; the fluorescent light emitted from the living tissue 1 upon the irradiation thereof by the excitation light passes through the image propagating optical system 24, the fluorescent light transmitting filter D of the rotating filter 25 and the mosaic filter 29, and is focused and received as a fluorescent image on the light receiving surface 28. The received fluorescent image is photoelectrically converted by the photoelectric converting element 27 and outputted from the light receiving means 20 as a fluorescent image analog signal representing a fluorescent image.

The fluorescent image analog signal outputted from the light receiving means 20 is inputted to the amplifying means 30, and outputted therefrom. The gain of the amplifying means 30 at this time is set in synchronization with the timing of the gain setting signals outputted from the control means 60; the gain by which the fluorescent image analog signal is to be amplified is set so as to be a larger gain than that by which the standard image has been amplified.

The amplified fluorescent image analog signal outputted from the amplifying means 30 is inputted to the A/D converting means 40, and after being converted thereby to a 12-bit fluorescent image digital signal representing the fluorescent image, is input to the computed visible image outputting means 61.

The computed visible image outputting means 61 into which the fluorescent image digital signal has been inputted records the fluorescent image digital signal obtained after said inputted fluorescent image digital signal has been passed through the narrow band transmitting filter M of the mosaic filter 29 as a narrow band fluorescent digital signal, and the fluorescent image digital signal obtained after said inputted fluorescent image digital signal has been passed through the wide band transmitting filter N of the mosaic filter 29 as a wide band fluorescent digital signal.

Here, the operation whereby the amplified fluorescent analog signal, which has been amplified by a gain larger than the gain used to amplify the standard image, is converted to digital values will be explained in detail.

As shown in FIG. 4, if the horizontal axis represents the values of the analog signal outputted from the amplifying means 30 and the vertical axis represents the digital values to which said analog values have been converted by the A/D converting means 40, the relation between the values of the standard image analog signal and the digital values to which said standard image analog signal has been converted by the A/D converting means 40 is shown by the straight line L1; if the largest value among the values of the standard image analog signal is designated as X1, this largest value X1 of the standard image analog signal is converted to a digital value Y1, which is close to the largest digital value to which said value X1 is capable of being converted.

For cases in which the fluorescent image analog signal has been amplified by the same gain as that used to amplify the standard image analog signal, the relation between the values of the fluorescent image analog signal and the values of the fluorescent image digital signal is shown by the same straight line L1 as that described above; if the largest value among the values of the fluorescent image analog signal, which is formed of signal values smaller than those forming the standard image analog signal, is designated as X2, this value X2 is converted to a digital value Y2, which is smaller than the value Y1.

However, the combined dynamic range of this fluorescent image analog signal and standard image analog signal is on the order of 90 dB, the gradations thereof will be lost unless said fluorescent image analog signal and standard image analog signal are converted to 16-bit digital values. That is to say, because a signal having the number of gradations corresponding to a 16-bit digital value (approximately 65,000 gradations) are to be converted to a 12-bit digital value (which has approximately 4000 gradations), a number of gradations equivalent to a 4-bit digital value are lost; whereby for cases in which the fluorescent image analog signal represents the number of gradations corresponding to a 12-bit digital value (approximately 4000 gradations), then only a number of gradations corresponding to an 8-bit digital value (approximately 250 gradations) can be represented when said fluorescent image analog signal is converted to digital values.

On the other hand, if the amplifying means 30 amplifies the fluorescent image analog signal by a gain larger than the gain used when amplifying the standard image analog signal, the relation between the values of the fluorescent image analog signal and the digital values to which said fluorescent image analog signal are converted is shown by the straight line L2, in which the analog values are shown to have been converted to larger digital values. In this manner, the loss of gradations in the fluorescent image represented by the fluorescent image analog signal when said fluorescent image analog signal is converted to digital values wherein the relation between said analog signal and said digital values is shown by the straight line L1 can be recovered.

If a conversion is performed, for example, wherein the straight line L1 represents the relation between a fluorescent image analog signal and the digital values to which said analog signal is converted, the largest value X2 of said analog signal is converted to an 8-bit (approximately 250 gradations) digital value (indicated as Y2 in FIG. 4). However, if the gain of the amplifying means 30 is set so that the largest value of the fluorescent image analog signal becomes substantially equivalent to the largest value of the standard image analog signal, when converted to digital values, the relation between said fluorescent image analog signal and the digital values to which said fluorescent image analog signal is converted is shown by the straight line L2; wherein, the largest value X2 of the fluorescent analog signal can be converted to a 12-bit (approximately 4000 gradations) digital value (indicated as Y3 in FIG. 4).

Note that the gain of the amplifying means 30 during the conversion of the fluorescent analog signal is not necessarily limited to being set at a value whereby the largest value of the fluorescent image analog signal becomes substantially equal to the largest value of the standard image analog signal, as long as the gain utilized when the fluorescent image analog signal is to be amplified is set larger than the gain utilized when the standard image analog signal is amplified.

After the fluorescent image analog signal has been converted to digital values as described above, said digital values are recorded in the computed visible image outputting means 61; said computed visible image outputting means 61 computes the ratio of the narrow band fluorescent image digital signal to the wide band fluorescent image digital signal, and forms a standardized visible fluorescent image signal representing a standardized fluorescent light intensity. Meanwhile, the computed visible image outputting means 61 forms a color visible image, which is a standard observation image representing a standard image, from the standard image digital signal representing a three color, red, blue and green standard image, and then outputs a visible image signal combining the standard observation color image signal and the standardized visible fluorescent image signal; said outputted visible image signal is displayed on the display device 62 as an image in which diagnostic data of the living tissue is represented.

Note that as to the technique for amplifying the analog signal representing the fluorescent image by a larger gain than that utilized to amplify the analog signal representing the standard image, a method such as that described below can be employed.

That is to say, a method wherein: the gain used when amplifying the analog signal representing the fluorescent image (hereinafter referred to as the fluorescent image gain) and the gain used when amplifying the analog signal representing the standard image (hereinafter referred to as the standard image gain) are each set to predetermined gains (or predetermined gain ranges) so that the fluorescent image gain is larger than the standard image gain; the fluorescent image gain is employed when the analog signal representing the fluorescent image is to be amplified, and the standard image gain is employed when the analog signal representing the standard image is to be amplified based on the timing of a gain setting signal output by the control means 60, can be employed as the means for amplifying the analog signal representing the fluorescent image by a larger gain than that utilized to amplify the analog signal representing the standard image. This means differs from a means such as an automatic gain controller (AGC), which automatically adjusts the amplification gain of the analog signal representing a photoelectrically converted image converted after the input of the image data representing the image before the photo-electrical conversion thereof, based on the image data of said converted image.

Note that the same effect described above can be obtained even if this fluorescent endoscope apparatus 100 is an endoscope apparatus provided with an amplifying means that has a fixed, uniform value for the gain thereof, and an A/D converting means for converting the fluorescent image analog signal to digital values having a narrower input range than that of the standard analog signals which are to be converted to digital values.

Figure 5:
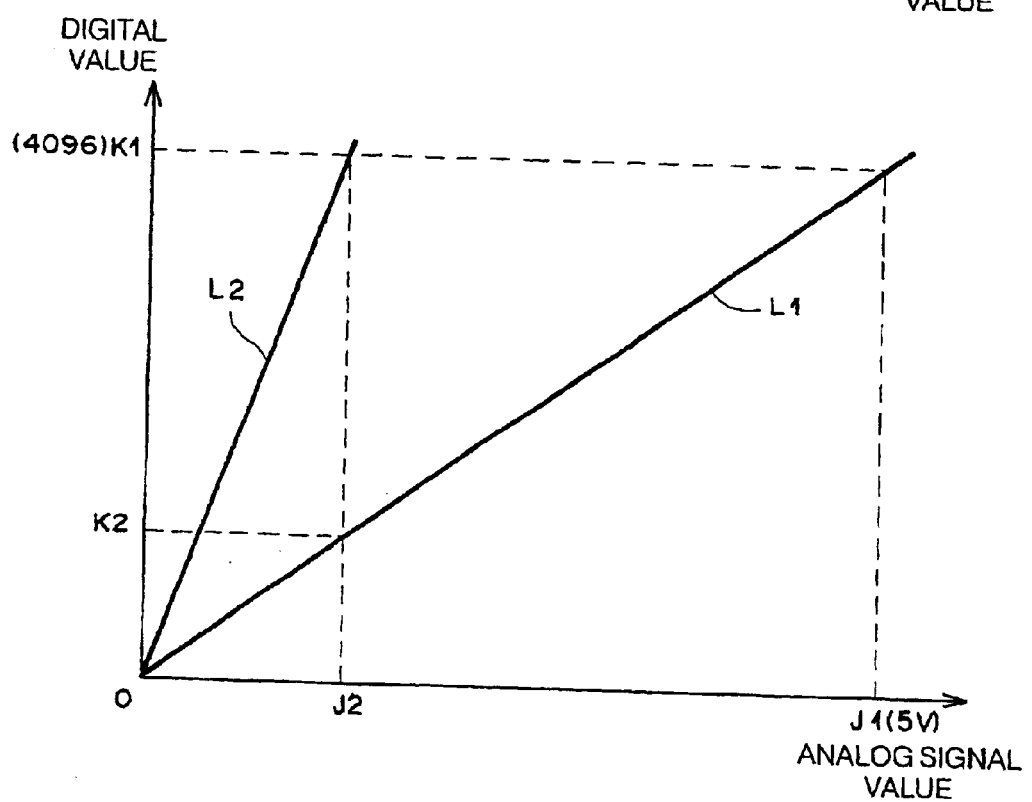
FIG. 5 is a graph illustrating the relationship between an analog signal and the digital values to which said analog signal is converted.

That is to say, as shown in FIG. 5, if the horizontal axis represents the values of the analog signals outputted from the amplifying means 30 and the vertical axis represents the digital values to which said analog signals have been converted by the A/D converting means 40, for a case in which the input range of the A/D converting means 40 is J1, the relation between the values of the standard image analog signal and the digital values to which said standard image analog signal has been converted by the A/D converting means 40 is shown by the straight line L1; wherein the relation between an analog signal having a value of J1 and the largest digital value K1 to which said value J1 is capable of being converted by the A/D converting means 40 is shown by said straight line L1.

For cases in which the fluorescent image analog signal is converted using the same input range as that with which the standard image analog signal is converted, the relation between the values of the fluorescent image analog signal and the values of the fluorescent image digital signal is shown by the same straight line L1 as that described above; if the largest value among the values of the fluorescent image analog signal, which is formed of signal values smaller than those forming the standard image analog signal, is designated as J2, this value J2 is converted to a digital value K2, which is smaller than the value K1.

On the other hand, if the input range to which the fluorescent image analog signal is to be A/D converted is made narrower than the input range to which the standard image analog signal is to be converted, and said input range of the A/D converted fluorescent image digital signal is designated as J2, the relation between the analog signal and the digital signal to which said analog signal is converted, wherein said analog signal is converted to larger digital values, is shown by the straight line L2; the analog signal having the value J2 is converted to the largest digital value K1.

More specifically, for a case in which the input range of a 12-bit A/D converting means is set at 0–5 V, analog signals in the range of 0–5 V are converted to digital values in the range of 0–4096; however, if the input range is set as a narrower range of 0–1 V, the analog signals in the range of 0–1 V are converted to digital values in the range of 0–4096. Utilizing a conversion relationship such as that described above, by setting the input range when the fluorescent image analog signal is to be A/D converted to an input range of 0–1 V, and the input range when the standard image analog signal is to be A/D converted to an input range of 0–5 V, the fluorescent image analog signal can be made to correspond to digital values of a higher order region.

Note it is not necessarily required that the input range utilized when the A/D converting means 40 is to convert the fluorescent image analog signal be set so that the largest value of the fluorescent image analog signal becomes substantially equal to the largest value of the standard image analog signal, as long as the input range utilized when the fluorescent image signal is to be converted by the A/D converting means 40 is set so that said input range is narrower than the input range utilized when the standard image is to be converted by the A/D converting means 40.

Figure 6:
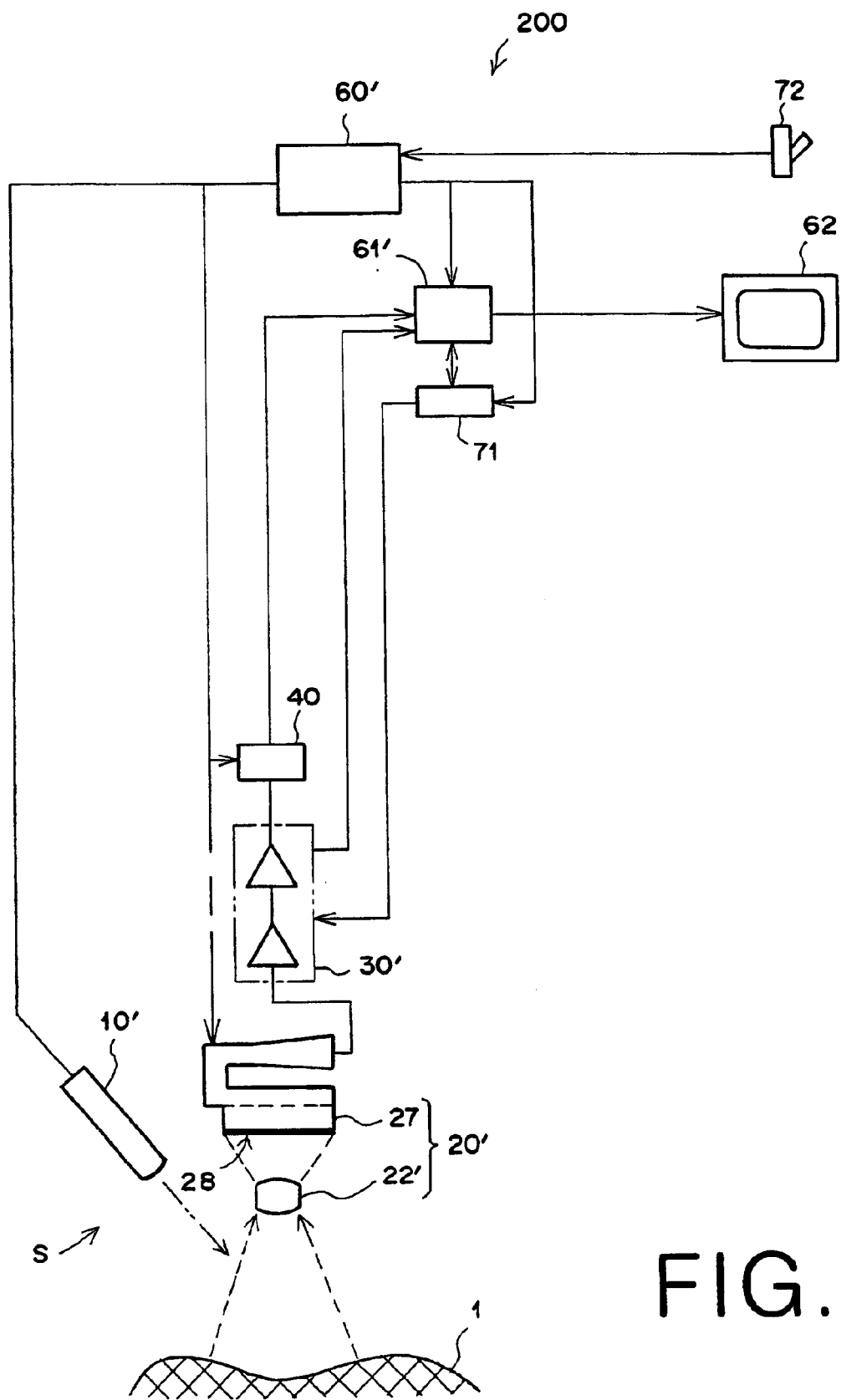
FIG. 6 is a block diagram of the configuration of the second embodiment of the present invention.
Figure 7:
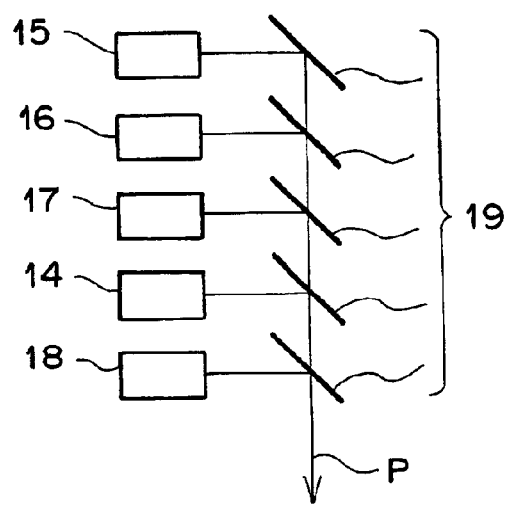
FIG. 7 is a magnified view showing the details of an illuminating means.

FIG. 6 is a block diagram of the configuration of the second embodiment of an endoscope apparatus according to present invention. The endoscope apparatus according to the first embodiment comprises: a photoelectric converting element, an amplifying means and an A/D converting means disposed within the distal end portion of the endoscope apparatus; wherein the display of a visible image representing a fluorescent image, a visible image representing an fluorescent light yield, and a visible image representing a standard observation image is switched between by use of an external switch disposed on the main body of the endoscope apparatus. Hereinafter, elements in common with the endoscope apparatus according to the above described first embodiment are likewise labeled, and further explanation thereof is omitted in so far as it is not particularly required.

The endoscope apparatus 200 according to the present invention comprises: an illuminating means 10' for irradiating a living tissue 1 with an illuminating light and an excitation light, each being emitted at a mutually different timing; a light receiving means 20' for receiving a fluorescent image formed of the fluorescent light emitted from the living tissue upon the irradiation thereof by the excitation light and a standard image formed of the reflected light reflected from the living tissue upon the irradiation thereof by the illuminating light, and photoelectrically converting the aforementioned standard image and the aforementioned fluorescent image received thereby to respective analog signals and outputting said analog signals; an amplifying means 30' for amplifying the analog signals; and an A/D converting means 40 for converting the amplified analog signals from the amplifying means 30 to respective 12-bit digital values. Note that the light receiving means 20', the amplifying means 30', and the A/D converting means 40 are disposed in the distal end portion S of the endoscope apparatus.

The illuminating means 10' is disposed in the distal end portion S of the endoscope apparatus, and comprises: a gallium nitride semiconductor laser (GaN-LD) 14 that emits pulse type excitation light having a wavelength near 410 nm; a red LED 15, a green LED 16, and a blue LED 17 for sequentially emitting onto the target tissue a red light, a green light, and blue light, which serve as illuminating light; and a semiconductor laser (GaAs-LD) 18 that emits a reference light (e.g., a near infrared light or a red light), which also serves as an illuminating light; further comprising a dichroic mirror 19 that reflects and transmits each of the emitted lights, which are reflected in the direction indicated by the arrow mark P in FIG. 6, said dichroic mirror 19 being provided with different reflecting and transmitting characteristics for each of said lights; wherein each said light is emitted at a different timing under the control of the control means 60' described below.

The light receiving means 20' comprises: a focusing optical system 22'; and a charge multiplying photoelectric converting element 27, which is formed of a plurality of pixels, for receiving and converting the image focused by the focusing optical system 22'; wherein the image of the living tissue 1 that has been focused the light receiving surface 28 of the photoelectric converting element 27 is photoelectrically converted and outputted as an analog signal.

Note that an excitation light cutoff filter, which cuts off the excitation light and transmit light having a wavelength in the visible spectrum exceeding the wavelength of the excitation light, is disposed on the light receiving surface 28 of the photoelectric converting element 27, which is formed of a plurality of pixels.

The gain of the amplifying means 30' is set in synchronization with the timing of the gain setting signals outputted from a histogram analyzing means 71, to be described below.

A computed visible image outputting means 61', into which the digital values outputted from the A/D converting means 40 are inputted, forms a fluorescent yield visible image signal representing the fluorescent light yield of the living tissue, a color visible image signal representing the living tissue and a fluorescent visible image signal representing the fluorescent light emitted from the living tissue, and outputs these formed image signals. The outputted images signals are displayed on the display device 62.

The switching between the display of the fluorescent light yield visible image, the color visible image, and the fluorescent light visible image on the display device 62 is performed by use of an external switch 72.

The control means 60' controls the overall operation of the apparatus (e.g., the emission of the excitation light, the sequential three color light and the reference light by the illuminating means 10', the photoelectrical conversion performed by the light receiving means 20, the output of the gain setting signals from the histogram analyzing means 71, etc.) so that the visible image selected by the external switch 72 is displayed on the display device 62.

Note that the circuitry of the computed visible image outputting means 61', which is down line from the A/D converting means 40, is formed of circuits and elements having a narrower dynamic range than that of the analog signals outputted from the light receiving means 20.

Next, the operations occurring in the above-described second embodiment will be explained.

For cases in which a color image representing a standard observation image is to be displayed on the display device 62, the external switch 72 is switched to the color visible image displaying position. Upon the execution of said switching operation, the sequential three color red, green and blue lights are emitted from the illuminating means 10' and projected onto the living tissue 1, and a three color RGB image digital signal formed of 12 bits of data representing a red, green, and blue standard observation image is recorded in the computed visible image outputting means 61' by the same operation as occurred in the first embodiment.

The computed visible image outputting means 61', which has recorded the RGB image digital signal, forms and outputs a color visible image signal based on this RGB image digital signal, and a color visible image representing a standard observation image is displayed on the display device 62.

Further, for cases in which a fluorescent visible image is to be displayed on the display device 62, the external switch 72 is switched to the fluorescent visible image displaying position. Upon the execution of said switching operation, the excitation light is emitted from the illuminating means 10' and projected onto the living tissue 1, and a fluorescent image digital signal formed of 12 bits of data is recorded in the computed visible image outputting means 61' by the same operation described above.

The computed visible image outputting means 61', which has recorded the fluorescent image digital signal, forms and outputs a fluorescent visible image signal based on this fluorescent image digital signal, and a visible image representing the fluorescent light emitted from the living tissue is displayed on the display device 62.

Further, for cases in which a fluorescent light yield visible image representing the fluorescent light yield of the living tissue 1 is to be displayed on the display device 62, the external switch 72 is switched to the fluorescent light yield visible image displaying position. Upon the execution of said switching operation, the excitation light and the reference light are emitted from the illuminating means 10', each being emitted at different timings, and projected onto the living tissue 1, and a fluorescent image digital signal formed of 12 bits of data and a reference image digital signal formed of 12 bits of data are recorded in the computed visible image outputting means 61' by the same operation described above.

The computed visible image outputting means 61', which has recorded the fluorescent image digital signal and the reference image digital signal, computes the ratio between the fluorescent image digital signal and the reference image digital signal and forms and outputs a fluorescent light yield visible image signal based on said ratio, and a visible image representing the fluorescent light yield is displayed on the display device 62.

Note that the size of the gain of the amplifying means 30' when the fluorescent image digital signal and the reference image digital signal are obtained is transmitted from the amplifying means 30' to the computed visible image outputting means 61', and is corrected so that an accurate value is obtained when the ratio between the fluorescent image digital signal and the reference image digital signal is computed.

The setting of the gain of the amplifying means 30' when these digital signals are to be obtained is performed by the gain setting signals outputted from the histogram analyzing means 71; these gain setting signals are set as follows.

When each of the RGB image digital signal, the fluorescent image digital signal, and the reference image digital signal are inputted to the computed visible image outputting means 61', these signals are transmitted from the computed visible image outputting means 61' to the histogram analyzing means 71; the histogram analyzing means 71 forms a histogram representing the light intensity distribution of each received image from the plurality of digital values corresponding to each pixel composing each digital signal. The histogram analyzing means 71 outputs setting signals to the amplifying means 30' so that the amplifying means 30' sets a high gain for cases in which the largest value of a formed histogram is less than a predetermined threshold value, and a low gain for cases in which the largest value of a formed histogram is greater than or equal to a predetermined threshold value.

That is to say, the gain of the amplifying means 30' is switched between two levels according to change of the intensity of the light received by the light receiving means 20': from extremely weak light intensity fluorescent light to high light intensity illuminating light, or the reverse, from high light intensity illuminating light to extremely weak light intensity fluorescent light.

Here, the operation occurring when the gain setting signals are output from the histogram analyzing means 71 when an RGB digital signal, a fluorescent image digital signal, and a reference image digital signal are to be obtained will be explained in detail.

Figure 8:
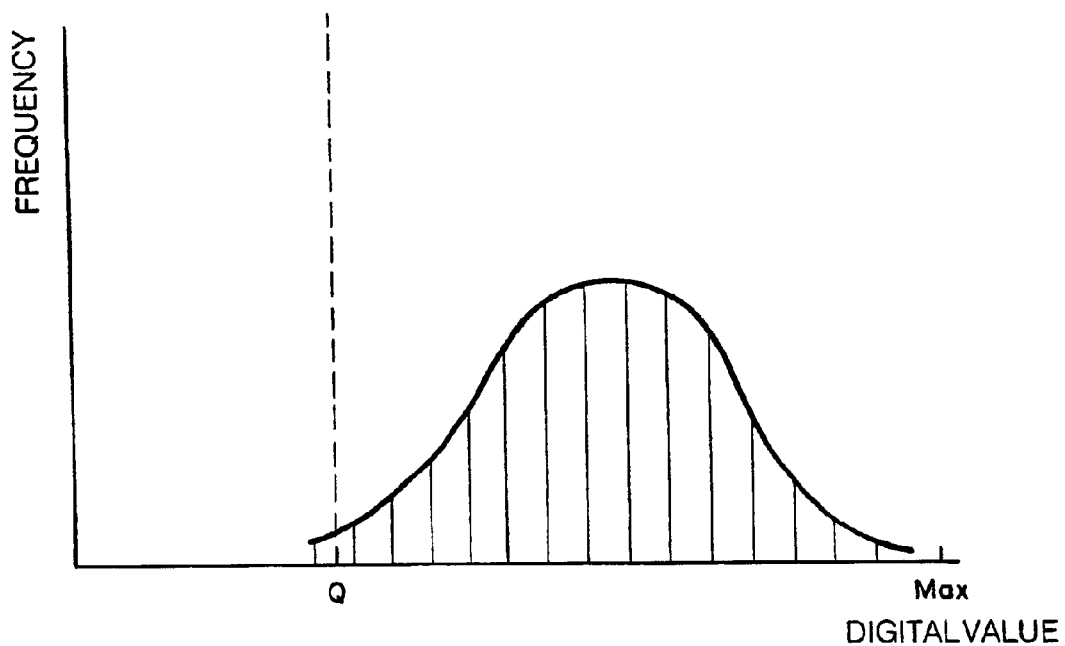
FIG. 8 is a graph showing the histogram of the digital values of a standard image.
Figure 9:
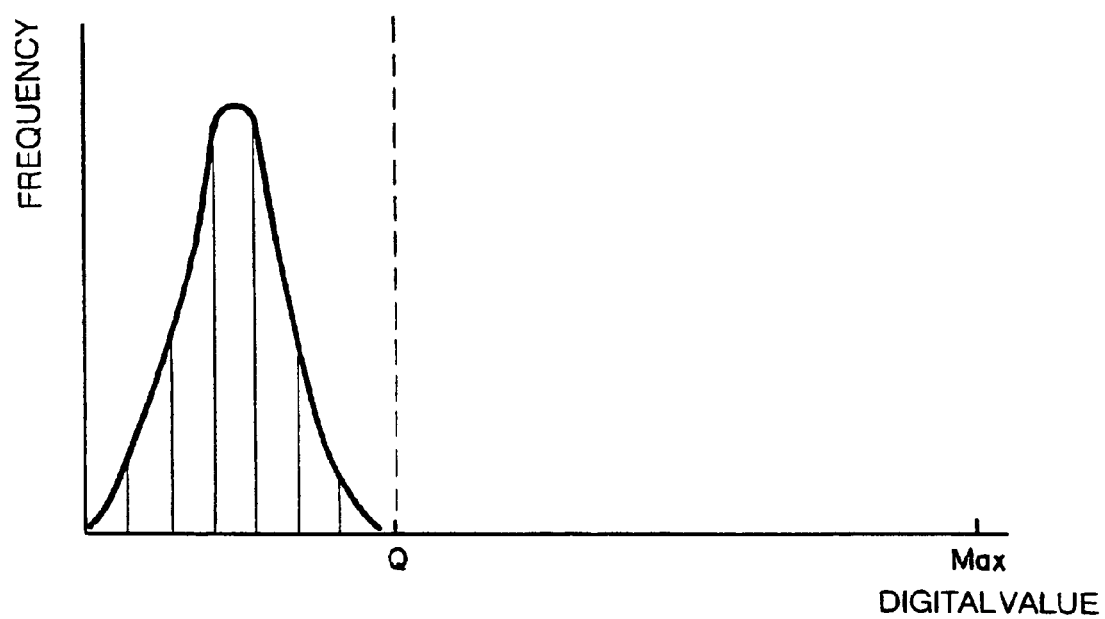
FIG. 9 is a graph showing the histogram of the digital values of a fluorescent image.

If the horizontal axis is designated as the digital values outputted from the amplifying means 30' and the vertical axis as the occurrence frequency of these digital values, if a histogram for an RGB image digital signal, which is a reference image digital signal, or a reference image digital signal is formed, as shown in FIG. 8, this histogram has a distribution consisting of occurrence frequencies tending toward the larger values on the digital values side, and the largest value of the distribution of said histogram is greater than or equal to the predetermined threshold value Q. On the other hand, a histogram of a fluorescent image digital signal has a distribution consisting of occurrence frequencies tending toward the smaller values on the digital values side, as shown in FIG. 9, and the largest value of the distribution of said histogram is less than the predetermined threshold value Q.

For cases in which the largest value of the distribution of the histogram of the digital signal representing each image inputted to the histogram analyzing means 71 is determined to be less than the predetermined threshold value Q, the histogram analyzing means 71 outputs setting signals to the amplifying means 30' so that the gain of this amplifying means 30' is set as a high gain (refer to L2 of FIG. 4); wherein the gain of the amplifying means 30' is set to a higher gain than that utilized in amplifying a standard image analog signal. On the other hand, for cases in which the largest value of the distribution of the histogram of the digital signal representing each image inputted to the histogram analyzing means 71 is determined to be greater than or equal to the predetermined threshold value Q, the histogram analyzing means 71 outputs setting signals to the amplifying means 30' so that the gain of this amplifying means 30' is set as a low gain (refer to L1 of FIG. 4); wherein the gain of the amplifying means 30' is set to a lower gain than that utilized in amplifying a fluorescent image analog signal.

Note that the determination by the histogram analyzing means 71 as to whether or not the largest value of the distribution of a histogram is greater than or equal to the predetermined threshold value Q is performed after a digital signal has been inputted thereto, therefore immediately after the external switch 72 has been changed to a different position and the type of light emitted from the illuminating means 10' changed thereby, the gain of the amplifying means 30' is not set at an appropriate value, and one-frame of the visible image signal portion is formed based on the analog signal not amplified by the appropriate gain; this one-frame visible of the image signal portion is not outputted from the computed visible image outputting means 61' and is not displayed.

Further, when a fluorescent light yield visible image is to be displayed, the excitation light and the reference light are each emitted at different timings, and the fluorescent image analog signal and the reference image analog signal are outputted alternately from the light receiving means. Then, the histogram analyzing means 71 into which these analog signals are inputted would alternately output gain setting signals that cause the gain of the amplifying means 30' to be set as a low gain and gain setting signals that cause the gain of the amplifying means 30' to be set as a high gain. However, in this case, the histogram analyzing means 71 recognizes from the change in the inputted digital value that the external switch 72 has been switched to the position of the fluorescent light yield visible image setting, corrects the timing of the output of the setting signals for setting the amplifying means 30' at a low gain or a high gain, and outputs said setting signals so that the alternately inputted fluorescent image analog signal and reference image analog signal are amplified by the appropriate gain. Further, in the same manner as described above, the visible image signal portion formed based on the analog signal not amplified by the appropriate gain is not outputted from the computed visible image outputting means 61' and is not displayed.

Note that the gain of the amplifying means 30' is set in a continuous, and not in a stepped manner; wherein a configuration may be adopted so that the largest value statistically obtained by measuring the distribution of the digital values of the respective histogram representing each type of image (a standard observation image, a fluorescent image and a reference image) in advance, is recorded in the histogram analyzing means 71, and the histogram analyzing means 71 outputs the gain setting signals to the amplifying means 30' so that the largest value of the distribution of the digital values representing each of the aforementioned images that have been inputted to and formed by the histogram analyzing means 71 is always equivalent to the statistical largest value.

Note that the same effect described above can be obtained even if this fluorescent endoscope apparatus 200 is an endoscope apparatus provided with an amplifying means of which the gain thereof is a fixed uniform value, and an A/D converting means for converting the fluorescent image analog signal to digital values having a narrower input range than that for the standard image analog signal to be converted to digital values.

According the present invention as described above, a photoelectrically converted and outputted analog signal can be converted to digital values having a narrower dynamic range while the reduction of the gradations thereof is suppressed, whereby the noise becoming mixed with the digital values can be controlled and the cost of the apparatus can also be reduced.

What is claimed is:

1. An image obtaining method for use in an endoscope apparatus, comprising the steps of:

irradiating a living tissue with an illuminating light and an excitation light, each of which is emitted at a mutually different timing, receiving, by use of a single photoelectric converting element, a fluorescent image formed of the fluorescent light emitted from the living tissue upon the irradiation thereof by the excitation light and a standard image formed of the reflected light reflected from the living tissue upon the irradiation thereof by the illuminating light, photoelectrically converting said received standard image and said received fluorescent image to obtain each as respective analog signals, converting, by use of an A/D converting means, said analog signals to respective digital values, and outputting said digital values as respective image signals, wherein said A/D converting means converts said analog signal representing the fluorescent image to digital values with a narrower input range than that with which the analog signal representing the standard image is converted.

2. An image obtaining apparatus for use in an endoscope apparatus comprising:

an illuminating means for irradiating a living tissue with an illuminating light and an excitation light, each of which is emitted at a mutually different timing, a light receiving means for receiving a fluorescent image formed of the fluorescent light emitted from the living tissue upon the irradiation thereof by the excitation light and a standard image formed of the reflected light reflected from the living tissue upon the irradiation thereof by the illuminating light, and photoelectrically converting said received standard image and said received fluorescent image to analog signals representing said received standard image and said received fluorescent image and outputting said analog signals, an amplifying means for amplifying said analog signals, and an A/D convening means for converting said amplified analog signals to respective digital values, wherein said A/D converting means is a means for convening said analog signal representing the fluorescent image to digital values with a narrower input range than that with which said analog signal representing the standard image is converted.

3. An image obtaining apparatus for use in an endoscope apparatus as defined in claim 2, Wherein said converting means is provided so as to be capable of switching the input range so that the largest value of the digital values representing the fluorescent image becomes substantially equal to the largest value of the digital values representing the standard image.

4. An image obtaining apparatus for use in an endoscope apparatus as defined in either of claim 2 or 3, wherein the input range is set based on respective histograms, which have been formed using digital values, representing the distribution of the light intensity of the fluorescent image and the standard image, so that the largest value of the light intensity distribution occurring within each histogram become substantially equal.

5. An image obtaining apparatus for use in an endoscope apparatus as defined in either of the claim 2 or 3, wherein the input range is selected from among a plurality of preset stepped values.

6. An image obtaining apparatus for use in an endoscope apparatus as defined in either of the claim 2 or 3, wherein the fluorescent image can be a fluorescent image formed of a plurality of mutually different wavelength ranges of fluorescent light, into each of which fluorescent light has been divided spectrally in a time division manner.

7. An image obtaining apparatus for use in an endoscope apparatus as defined in either of the claim 2 or 3, wherein the illuminating light is a light containing wavelengths within the near infrared wavelength range.

8. An image obtaining apparatus for use in an endoscope apparatus as defined in either of the claim 2 or 3, wherein the A/D converting means is a means for converting the analog signal outputted from the amplifying means to a digital value containing 14 bits or less of data.

9. An image obtaining apparatus for use in an endoscope apparatus as defined in either of the claim 2 or 3, wherein the light receiving means is a charge multiplying photo-electric converting element.

* * * * *